(12) United States Patent
Bara

(10) Patent No.: US 6,238,651 B1
(45) Date of Patent: May 29, 2001

(54) POLISH COMPOSITION FOR NAIL MAKEUP AND/OR CARE CONTAINING A VOLATILE FLUORINATED COMPOUND

(75) Inventor: Isabelle Bara, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/343,518

(22) Filed: Jun. 30, 1999

(30) Foreign Application Priority Data

Jun. 30, 1998 (FR) .................................................. 98 08340

(51) Int. Cl.$^7$ ....................................................... A61K 7/04
(52) U.S. Cl. ................................................................ 424/61
(58) Field of Search ................................ 424/61; 524/24

(56) References Cited

U.S. PATENT DOCUMENTS 4,421,881 * 12/1983 Benkendorf et al. .................. 524/24

FOREIGN PATENT DOCUMENTS

9636689 * 11/1996 (WO) .

* cited by examiner

*Primary Examiner*—Thurman K. Page
*Assistant Examiner*—Blessing Fubara
(74) *Attorney, Agent, or Firm*—Oblon, Spivak, McClelland, Maier & Neustadt, P.C.

(57) ABSTRACT

A polish composition for nail makeup and/or care, comprising in an organic solvent system for polishes, a film-forming substance, optionally a plasticizing agent, and optionally a resin. The solvent system for polishes contains at least one volatile halogenated compound in which the halogen atoms are fluorine, that has a vapor pressure greater than 20 mba (2000 Pa) at 25° C. The composition may colorless or colored with a coloring agent. The composition is characterized by very rapid drying after application to the surface of nails.

26 Claims, No Drawings

POLISH COMPOSITION FOR NAIL MAKEUP AND/OR CARE CONTAINING A VOLATILE FLUORINATED COMPOUND

BACKGROUND OF THE INVENTION

1. Field of the Invention

The present invention relates to a polish composition containing a fluorinated organic compound and a film-forming substance. The present invention also relates to a process of treating nails by applying the topically applying the composition to nails.

2. Description of the Background

Users of nail polish are accustomed to preferably applying the polish in two successive layers to obtain good qualities of holding, brilliance, and shock resistance. However, between each application it is necessary to wait at least ten minutes before obtaining complete drying of the film both on the surface and in depth.

Thus, for several years research has been directed to the perfection of nail polishes that have much shorter drying times to meet a growing consumer demand for such products.

To accomplish this goal, different film-forming polymers have been considered. However, these materials produce rapid drying only on the surface.

It has also been suggested to use certain volatile oils, specifically silicone compounds such as cyclodimethicones or low-molecular-weight polydimethylsiloxanes, as well as hydrocarbon products such as isoparaffins and isododecane. However, these compounds have a number of drawbacks such as specifically low flash points, and some of them have a persistent disagreeable odor, thus limiting their use in the cosmetic field.

In addition to this problem of the rapidity of drying, the polish compositions must also impart good film-forming properties, and the film must present a homogeneous appearance and qualities of brilliance and resistance once it has dried.

SUMMARY OF THE INVENTION

It is an object of the present invention to provide a novel cosmetic polish composition for nail makeup and/or care.

It is another object of the invention to provide a composition that is characterized by very rapid drying after application to the surface of nails.

It is another object of the invention to provide a process of nail makeup and/or care.

It is another object of the invention to provide a process for accelerating the drying time of a cosmetic polish composition.

After numerous studies of various types of compounds, it has now been found that it was possible, by using volatile fluorinated compounds, to reduce very significantly the drying time of the film of polish while retaining good homogeneity and the qualities of brilliance and resistance. The volatile fluorinated compounds are well-suited for cosmetic polish compositions, since they are odorless and colorless, contrary to certain compounds previously known.

Accordingly, the objects of the invention, and others, may be accomplished with a polish composition, suitable as a nail makeup and/or for nail care, comprising:

a film-forming substance; and an organic solvent comprising at least one volatile halogenated organic compound, where the halogen atoms are fluorine atoms, i.e., a fluorinated organic compound, and where the compound has a vapor pressure greater than 20 mba (2000 Pa) at 25° C.

The objects of the invention may also be accomplished with a process for increasing the drying time of a nail care composition, comprising incorporating the fluorinated organic compound into a nail care composition, e.g., a nail polish, optionally containing other organic solvents, in order to reduce the time required for the composition to dry on the nail surface.

The objects of the invention may also be accomplished with a method of polishing nails, by applying the inventive composition to the nails.

The objects of the invention may also be accomplished with a method of polishing nails, by applying the inventive composition to the nails.

The objects of the invention may also be accomplished with a method of preparing the inventive composition by combining the film-forming substance the organic solvent.

A more complete appreciation of the invention and many of the attendant advantages thereof will be readily obtained as the same becomes better understood by reference to the following detailed description.

DETAILED DESCRIPTION OF THE INVENTION

The inventive composition may be colorless or colored. When colored, the composition contains at least one coloring agent. The composition may also contain a plasticizing agent and/or a resin.

The organic fluorinated compound has a vapor pressure greater than about 20 mba (2000 Pa) at 25° C. Preferably, the compound has a vapor pressure greater than 40 mba at 25° C.

The term "halogenated organic compound whose halogen is fluorine" refers to an organic compound having no halogen atoms other than fluorine atoms. Perfluorinated compounds may be used in the inventive composition.

The term "organic solvent" or "organic solvent system" refers to any non-aqueous medium liquid at room temperature (25° C.), comprising, for example, a ketone, glycol, ester, ether, alkane, or aromatic aldehyde compound. The term "solvent" includes single liquids as well as mixtures of different liquids at all proportions.

Among the volatile halogenated organic compounds, also called volatile fluorinated compounds, of the polish solvent system, and meeting the criterion of vapor pressure mentioned above, examples include:

(1) perfluorocycloalkyl compounds represented by the formula (1) below:

in which:

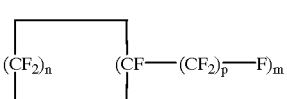

(I)

n is 4 or 5, m is 1 or 2, and p is 1, 2, or 3 provided that when m=2, the groups are not necessarily in the alpha position relative to one another, and (2) fluoroalkyl or heterofluoroalkyl compounds represented by the formula (II) below:

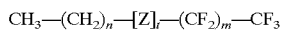

$$CH_3-(CH_2)_n-[Z]_t-(CF_2)_m-CF_3 \quad (II)$$

in which:

t is 0 or 1, n is 0, 1, 2, or 3, m is 2, 3, 4, or 5, and

Z is O, S, or NR, with R being hydrogen, a —$(CH_2)_n$—$CH_3$ radical, or —$(CF_2)_m$—$CF_3$.

Among the perfluorocycloalkyls of formula (I), preferred examples include perfluoromethylcyclopentane and perfluorodimethylcyclohexane, sold respectively under the names of "Flutec PC1®" and "Flutec PC3®" by BNFL FLUOROECHEMICALS Ltd.

Among the fluoroalkyl or heterofluoroalkyl compounds of formula (II), examples include methoxynonafluorobutane sold under the name "MSX 4518®" by the 3M Company (t=1, Z=O, n=0, and m=3), or ethoxynonafluorobutane sold under the name "HFE 7200" by the Archimex Company (t=1, Z=O, n=1, and m=3).

In the polish compositions of the invention, the solvent system may be present in a proportion between 50 and 90% by weight relative to the total weight of the polish, and the volatile fluorinated compound represents about 5 to 90% and preferably 10 to 50% of the total weight of the polish. This range for the amount of solvent includes all specific values and subranges therebetween, including 60, 70, 75, 80 and 85% by weight. The ranges for the amount of fluorinated compound includes all specific values and subranges therebetween, such as 8, 12, 15, 20, 30, 40, 60, 70 and 80% by weight.

Since the drying time of the polish compositions is a function of the concentration of volatile halogenated compound, it is possible to vary the drying time by varying the amount of the volatile halogenated compound.

Examples of the organic solvents that may comprise the solvent system of the polish, in addition to the volatile fluorinated compound, include acetone, methyl acetate, ethyl acetate, butyl acetate, amyl acetate, 2-methoxyethyl acetate, methyl ethyl ketone (MEK), methyl isobutyl ketone (MIK), isopropyl acetate, ethanol, isopropanol, ethylene glycol, propylene glycol, pentylene glycol, glycerol, decane, heptane, cyclohexane, benzaldehyde, diethyl ether, dimethyl ether, octane or toluene, xylene, n-butanol, n-propanol, and mixtures thereof.

In an embodiment of the invention, the solvent system may also contain volatile silicones, such as:

(1) low-molecular-weight linear polydimethylsiloxanes represented by the formula (III) below:

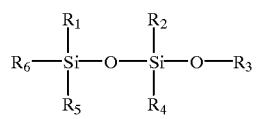

(III)

in which:

$R_1$ to $R_6$ are the same or different and represent a hydrogen atom, a hydroxyl group, or an alkyl or alkenyl $C_1$–$C_6$ radical;

(2) cyclic polydimethylsiloxanes represented by the formula (IV) below:

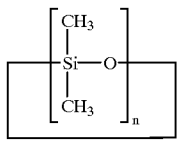

(IV)

in which n is 4, 5, or 6.

Among the compounds of formula (IV) example include octamethylcyclotetrasiloxane, decamethylcyclopentasiloxane, and dodecamethylcyclohexasiloxane.

The film-forming substance of the polishes is generally present in a proportion of about 5 to 20% and preferably about 10 to 20% by weight relative to the total weight of the polish composition. These ranges includes all specific values and subranges therebetween, including 8, 12, 15 and 18% by weight.

Examples of the film-forming substances include nitrocelluloses of the "RS" or "SS" type, and in particular type ¼ second RS nitrocellulose, type ½ second RS nitrocellulose, type Y2 second SS nitrocellulose, and type ¾ second RS nitrocellulose.

Other film-forming substances that may also be used are acrylic polymers or copolymers, acrylic resins, styrene resins, acrylate-styrene resins, and vinyl resins, vinyl copolymers, polyester polymers, and polyurethane polymers.

The plasticizing agent of the polishes pursuant to the invention may be present in a proportion between 2 and 15%, and preferably between 5 and 10% by weight relative to the total weight of the polish composition. These ranges includes all specific values and subranges therebetween, such as 3, 8 and 12% by weight. The plasticizing agents provide for adjustment of the flexibility of the film without weakening its resistance or physical strength.

Among the plasticizing agents that may be used in the cosmetic polish compositions pursuant to the invention, examples include: tributyl phosphate, tributoxyethyl phosphate, tricresyl phosphate, triphenyl phosphate, glycerol triacetate, butyl stearate, butyl glycolate, benzyl benzoate, butyl acetyltricinoleate, glyceryl acetyltricinoleate, dibutyl phthalate, diisobutyl phthalate, dioctyl phthalate, dimethoxyethyl phthalate, diamyl phthalate, triethyl citrate, tributyl citrate, tributyl acetylcitrate, tri(2-ethylhexyl) acetylcitrate, dibutyl tartrate, camphor, and mixtures thereof.

The polish compositions pursuant to the invention may also contain a resin in a proportion between 0.5 and 15%, and preferably between 5 and 10% by weight relative to the total weight of the composition. These ranges includes all specific values and subranges therebetween, such as 1, 2, 3, 8 and 12% by weight. These resins, while augmenting the film-forming power, improve brilliance and adhesion.

Among the numerous resins that can be used, preferred examples include resins of the arylsulfonamide-formaldehyde type or the arylsulfonamide-epoxy type, specifically toluenesulfonamide-formaldehyde resin better known by the commercial names of "Santolite MHP®", "Santolite MS 80%®, and "KetJenflex MS 80®", or alkyl resins such as those sold by the DAI NIPPON Company under the name "Beckosol ODE 230-70®".

When the compositions pursuant to the invention are colored, they can also contain organic or inorganic colorants and/or pigments, i.e., coloring agents.

Examples of the organic pigments that may be used are D&C Red No. 10, 11, 12, and 13, D&C Red No. 7, D&C Red No. 5 and 6, and D&D Red No. 34, as well as lakes such as D&C Yellow Lake No. 5 and D&C Red Lake No. 2. Examples of the inorganic pigments include titanium dioxide, bismuth oxychloride, brown iron oxide, and red iron oxides.

Generally, the colorants and/or pigments are present in the polish compositions pursuant to the invention in a proportion between 0.01 and 2% by weight relative to the total weight of the compositions. These ranges includes all specific values and subranges therebetween, including 0.02, 0.05, 0.1, 0.2, 0.5, 1, and 1.5% by weight. To prevent sedimentation of the pigments, certain thixotropic agents such as bentones can be used, such as for example "Bentone 27®" or "Bentone 38®".

The polish compositions pursuant to this invention can also contain conventional cosmetic ingredients and/or agents, in particular components active for nail treatment. Among them may be mentioned UVA and/or UVB filters, dispersing agents and moisteners, dulling agents, adhesion promoters, leveling agents, rheological agents such as pyrogenous silicones, antioxidants, preservatives, thickeners or gelling agents, and nail hardeners.

An aspect of the present invention is a process for preparing a polish composition with an organic solvent medium for nail makeup and/or care to accelerate the drying time, by introducing into the composition an effective quantity of at least one volatile halogenated solvent, whose halogen(s) are fluorine, that has a vapor pressure greater than 20 mba (2000 Pa) at 25° C., as described above.

The inventive composition may be used by topical application to nail surfaces. The methods of topical application of polish compositions to nails is well-known. For example, the composition may be applied with a brush. After application, the composition is allowed to dry.

Having generally described this invention, a further understanding can be obtained by reference to certain specific examples which are provided herein for purposes of illustration only and are not intended to be limiting unless otherwise specified.

EXAMPLES

Example 1

| Colored Nail Polish A colored nail polish is prepared by mixing the following ingredients: | |
|---|---|
| 30% nitrocellulose in isopropyl alcohol | 10 g |
| Ethyl acetate | 41 g |
| Methoxynonafluorobutane sold under the name MSX 4518 by the 3M Company | 20 g |
| Dibutyl phthalate | 15 g |
| Gelling agent | 1.5 g |
| Pigments | 1.5 g |
| Toluenesulfonamide-formaldehyde resin | 11 g |

This polish, with good fluidity, is easily applied to the nail surface and after a very short drying time it leads to the formation of a homogeneous film with good adhesion and beautiful luster.

Example 2

| Colorless Nail Polish A colorless nail polish is prepared by mixing the following ingredients: | |
|---|---|
| 30% nitrocellulose in isopropyl alcohol | 18.5 g |
| Ethyl acetate | 27.9 g |
| Methoxynonafluorobutane sold under the name MSX 4518 by the 3M Company | 19.2 g |
| Butyl acetate | 9.42 g |
| Isopropyl alcohol | 6.28 g |
| Tributyl acetylcitrate | 6.3 g |
| Toluenesulfonamide-formaldehyde resin | 11.00 g |
| Camphor | 1.4 g |

Obviously, numerous modifications and variations of the present invention are possible in light of the above teachings. It is therefore to be understood that within the scope of the appended claims, the invention may be practiced otherwise than as specifically described herein.

This application is based on French Patent Application Serial No. 98-08340, filed on Jun. 30, 1998, and incorporated herein by reference.

What is claimed is:

1. A polish composition, suitable as a nail makeup and/or for nail care, comprising:
   a film-forming substance selected from the group consisting of nitrocelluloses, acrylic polymers or copolymers, acrylic resins, styrene resins, acrylate-styrene resins, vinyl resins, vinyl copolymers, polyester polymers, and polyurethane polymers; and
   an organic solvent comprising at least one volatile halogenated organic compound, wherein the halogen atoms are fluorine atoms and wherein the compound has a vapor pressure greater than 20 mba (2000 Pa) at 25° C.

2. The composition of claim 1, which is colorless.

3. The composition of claim 1, further comprising at least one coloring agent.

4. The composition of claim 1, further comprising a plasticizing agent.

5. The composition of claim 1, further comprising a resin.

6. The composition of claim 1, wherein volatile halogenated compound is a perfluorocycloalkyl compound represented by formula (I):

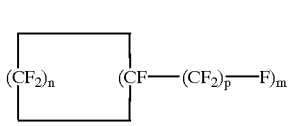

(I)

wherein
n is 4 or 5,
m is 1 or 2, and
p is 1, 2, or 3
provided that when m=2, the groups are not necessarily in the alpha position relative to one another.

7. The composition of claim 6, wherein the perfluorocycloalkyl compound is selected from the group consisting of perfluoromethylcyclopentane and perfluorodimethylcyclohexane.

8. The composition of claim 1, wherein the volatile halogenated compound is a fluoroalkyl or heterofluoroalkyl compound represented by formula (II):

(II)

wherein
t is 0 or 1,
n is 0, 1, 2, or 3,
m is 2, 3, 4, or 5, and
Z is O, S, or NR, wherein R is hydrogen, a —$(CH_2)_n$— $CH_3$ radical, or —$(CF_2)_m$—$CF_3$.

9. The composition of claim 8, wherein the heterofluoroalkyl compound is methoxynonafluorobutane or ethoxynonafluorobutane.

10. The composition of claim 1, comprising 50 and 90% by weight of the solvent.

11. The composition of claim 1, comprising 5 and 90% by weight of the volatile halogenated compound.

12. The composition of claim 1, wherein the solvent further comprises at least one organic solvent selected from the group consisting of acetone, methyl acetate, ethyl acetate, butyl acetate, 2-methoxyethyl acetate, methyl ethyl ketone (MEK), methyl isobutyl ketone (MIK), isopropyl acetate, isopropanol, ethanol, ethylene glycol, glycerol, and propylene glycol.

13. The composition of claim 1, wherein the organic solvent further comprises at least one volatile silicone selected from the group consisting of:

(a) low-molecular-weight linear polydimethylsiloxanes represented by formula (III):

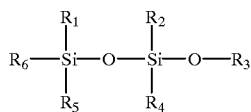

(III)

wherein n is 4, 5, or 6, and (b) cyclic polydimethylsiloxanes represented by formula (IV):

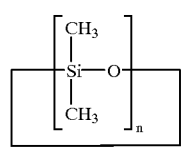

(IV)

wherein n is as defined above.

14. The composition of claim 13, wherein the compound represented by formula (IV) is selected from the group consisting of octamethylcyclotetrasiloxane, decamethylcyclopentasiloxane, and dodecamethylcyclohexasiloxane.

15. The composition of claim 1, comprising 5 and 20% by weight of the film-forming substance.

16. The composition of claim 4, comprising 2 and 15% by weight of the plasticizing agent.

17. The composition of claim 5, comprising 0.5 and 15% by weight of the resin.

18. The composition of claim 1, further comprising 0.01 and 2% by weight of at least one pigment and/or colorant.

19. The composition of claim 1, further comprising at least one selected from the group consisting of UVA filter, UVB filter, dispersing agent, moistener, dulling agent, adhesion promoter, leveling agent, rheological agent, pyrogenous silicone, antioxidant, preservative, thickener, gelling agent and nail hardener.

20. The composition of claim 5, wherein the plasticizing agent is selected from the group consisting of tributyl phosphate, tributoxyethyl phosphate, tricresyl phosphate, triphenyl phosphate, glycerol triacetate, butyl stearate, butyl glycolate, benzyl benzoate, butyl acetyltricinoleate, glyceryl acetyltricinoleate, dibutyl phthalate, diisobutyl phthalate, dioctyl phthalate, dimethoxyethyl phthalate, diamyl phthalate, triethyl citrate, tributyl citrate, tributyl acetylcitrate, tri(2-ethylhexyl) acetylcitrate, dibutyl tartrate, camphor, and mixtures thereof.

21. The composition of claim 5, wherein the resin is selected from the group consisting of arylsulfonamide-formaldehyde resins, arylsulfonamide-epoxy resins, and alkyl resins.

22. A method of preparing the composition of claim 1, comprising combining the film-forming substance the organic solvent.

23. A method of polishing nails, comprising applying the composition of claim 1 to the nails.

24. A method of cosmetically treating nails, comprising applying the composition of claim 1 to the nails.

25. A method of forming a film on nails, comprising applying the composition of claim 1 to the nails.

26. A method of lowering the drying time of a nail polish and/or nail make-up composition, comprising incorporating into the composition an effective amount of at least one volatile halogenated organic compound, wherein the halogen atoms are fluorine atoms and wherein the compound has a vapor pressure greater than 20 mba (2000 Pa) at 25° C.

* * * * *